(12) United States Patent
Gutierrez et al.

(10) Patent No.: US 9,504,511 B2
(45) Date of Patent: *Nov. 29, 2016

(54) FLUID RECIRCULATION DEBRIS HANDLING SYSTEM

(71) Applicant: Boston Scientific Scimed, Inc., Maple Grove, MN (US)

(72) Inventors: Eric Gutierrez, Bedford, TX (US); Steve Tylicki, Oxford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 255 days.

This patent is subject to a terminal disclaimer.

(21) Appl. No.: 14/314,885

(22) Filed: Jun. 25, 2014

(65) Prior Publication Data

US 2014/0309629 A1    Oct. 16, 2014

Related U.S. Application Data

(63) Continuation of application No. 12/493,793, filed on Jun. 29, 2009, now Pat. No. 8,790,334.

(60) Provisional application No. 61/100,972, filed on Sep. 29, 2008.

(51) Int. Cl.
*A61B 18/14* (2006.01)
*A61B 18/04* (2006.01)
*A61M 1/00* (2006.01)

(52) U.S. Cl.
CPC ............ *A61B 18/04* (2013.01); *A61M 1/0058* (2013.01); *A61M 1/0084* (2013.01); *A61B 2018/046* (2013.01); *A61M 2210/1433* (2013.01)

(58) Field of Classification Search
CPC .. A61B 18/04; A61B 18/08; A61B 18/1302; A61B 18/1492; A61B 18/148; A61B 2217/005; A61B 2217/007; A61M 1/0058; A61M 1/0084; A61M 2210/1433
See application file for complete search history.

(56) References Cited

U.S. PATENT DOCUMENTS

| | | | | |
|---|---|---|---|---|
| 4,676,258 A | * | 6/1987 | Inokuchi | A61N 1/403 607/154 |
| 5,449,380 A | * | 9/1995 | Chin | A61B 18/08 604/96.01 |
| 5,451,208 A | * | 9/1995 | Goldrath | A61B 18/00 600/135 |
| 5,827,218 A | * | 10/1998 | Nguyen | A61M 1/0084 137/860 |
| 2004/0193150 A1 | * | 9/2004 | Sharkey | A61B 18/1402 606/41 |
| 2010/0305557 A1 | * | 12/2010 | Chu | A61B 1/012 606/27 |

* cited by examiner

*Primary Examiner* — Michael Peffley
(74) *Attorney, Agent, or Firm* — Fay Kaplun & Marcin, LLP

(57) ABSTRACT

A device for circulating fluid to a target site within a living body, comprises a longitudinal member including an inlet lumen supplying fluid to the target site and a return lumen withdrawing fluid from the target site, the return lumen surrounding the inlet lumen and a screen coupled to a distal end of the longitudinal member, the screen including a plurality of openings extending therethrough from a radially inner surface forming a radially outer wall of a distal portion of the return lumen to an outer surface thereof.

15 Claims, 4 Drawing Sheets

FLUID RECIRCULATION DEBRIS HANDLING SYSTEM

PRIORITY CLAIM

This application is a Continuation application of U.S. application Ser. No. 12/493,793, entitled "Fluid Recirculation Debris Handling System" filed on Jun. 29, 2009, now U.S. Pat. No. 8,790,334; which claims the priority to the U.S. Provisional Application Ser. No. 61/100,972, entitled "Fluid Recirculation Debris Handling System" filed on Sep. 29, 2008. The specification of the above-identified patent/application is incorporated herewith by reference.

BACKGROUND

Endometrial ablation is a procedure conducted to reduce or eliminate excessive uterine bleeding by ablating the innermost lining of the uterus, known as the endometrium. One method of ablating the endometrium is by using the HydroThermAblator® System (HTA) which circulates heated fluid in the uterus. A sheath is inserted into the uterus via the cervix to introduce and circulate the heated fluid and to maintain a target ablation temperature through the uterus. An ablation sheath generally includes an inlet lumen via which the heated fluid is introduced into the uterus and a return lumen via which the fluid may be returned, heated and circulated back into the body to maintain the target ablation temperature.

SUMMARY OF THE INVENTION

The present invention is directed to a device for circulating fluid to a target site within a living body, comprising a longitudinal member including an inlet lumen supplying fluid to the target site and a return lumen withdrawing fluid from the target site, the return lumen surrounding the inlet lumen and a screen coupled to a distal end of the longitudinal member, the screen including a plurality of openings extending therethrough from a radially inner surface forming a radially outer wall of a distal portion of the return lumen to an outer surface thereof.

DETAILED DESCRIPTION

Figure 1:
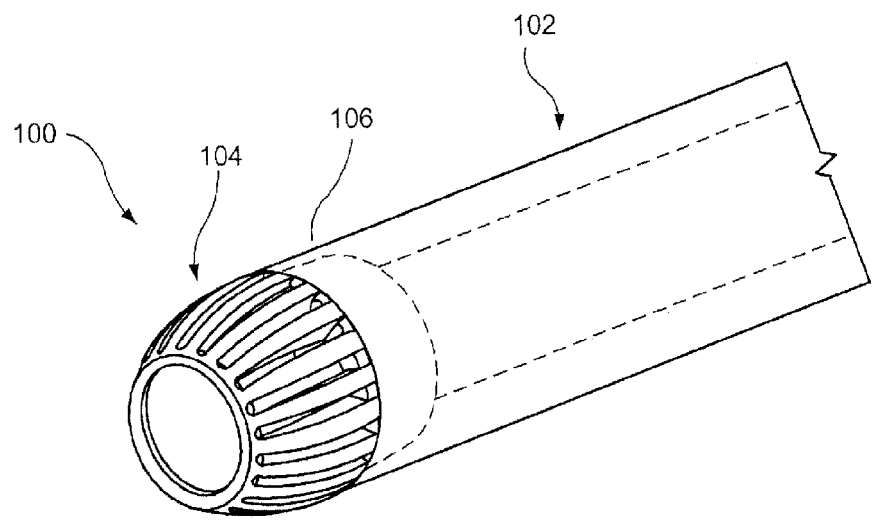
FIG. 1 shows a perspective view of a device according to a first exemplary embodiment of the present invention.

The present invention, which may be further understood with reference to the following description and the appended drawings, wherein like elements are referred to with the same reference numerals, relates to devices for treating an endometrial lining of a uterus. In particular, the present invention relates to devices for circulating heated fluid through hollow organs such as the uterus to treat tissue therein (e.g., the endometrium). As the endometrial lining is ablated, debris is often generated in the uterus. Exemplary embodiments of the present invention provide a device for circulating fluid, including a distal tip that prevents the debris from returning into and occluding the device, thereby preventing any impedance of the circulatory flow of the fluid. As would be understood by those skilled in the art, although this invention is described in conjunction with the ablation of the endometrium, the invention may be used in conjunction with the treatment of the tissue of any hollow organ.

Figure 2:
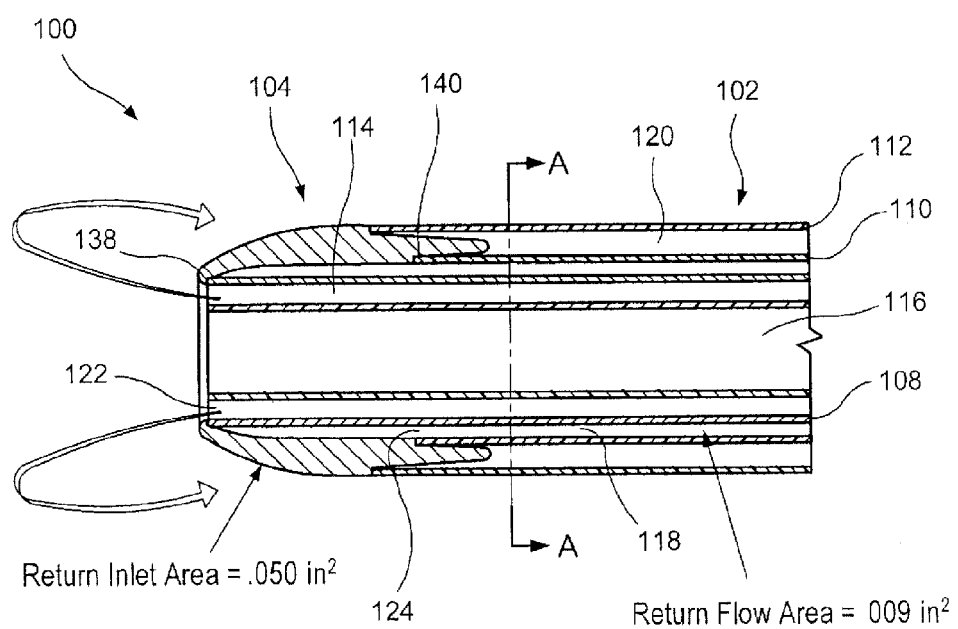
FIG. 2 shows a longitudinal cross-sectional view of the device of FIG. 1.
Figure 3:
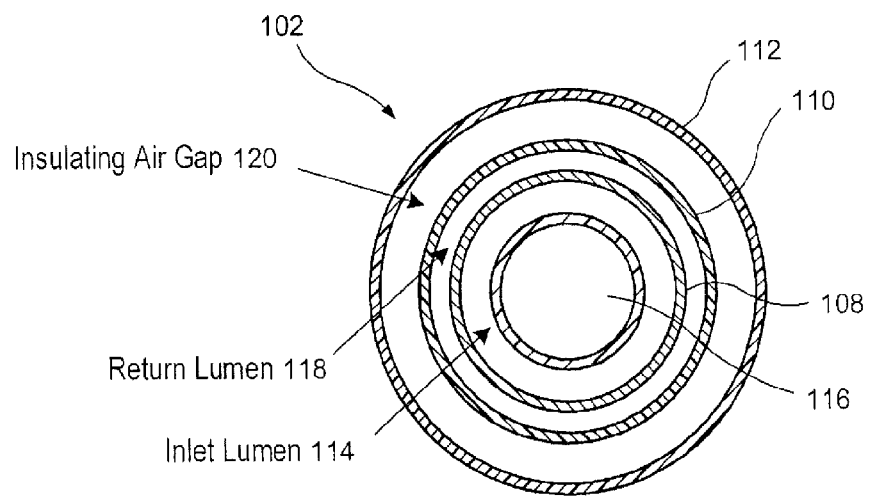
FIG. 3 shows a lateral cross-sectional view of the device of FIG. 1.

As shown in FIGS. 1-4, a device 100, according to an exemplary embodiment of the invention comprises a longitudinal member 102 and a screen 104 located at a distal end 106 thereof. The device 100 may be sized and shaped to be inserted into an internal space of a living body, in particular, to be inserted into a uterus via a cervix. In a preferred embodiment, an outer diameter of the device 100 may range from approximately 7.0 mm to 7.7 mm to ensure ease of insertion of the device 100 into the uterus via the cervix. As shown in FIGS. 2-3, the longitudinal member 102 comprises a first sleeve 108 housed within a second sleeve 110 which is housed within a third sleeve 112. The sleeves 108, 110, 112 in this example are co-axial. An inlet lumen 114 within the first sleeve 108 extends from a proximal end (not shown) connectable to a supply of ablation fluid so that, when in a desired position within the body, fluid introduced thereinto flows into the uterus via a distal opening 122. The first sleeve 108 may be formed of a metal such as, for example, stainless steel. It will be understood by those of skill in the art that the metal will provide mechanical stability and stiffness of the longitudinal member 102, while providing an optimal cross-sectional fluid flow area. A hysteroscope 116 may also be introduced into the body via the lumen 114 with fluid continuing to flow in an annular space between the hysteroscope and the wall of the lumen 114 as shown by the arrows in FIG. 2. The metal material of the first sleeve 108 guides a sometimes sharp tip of the hysteroscope 116 without catching on or damaging the material of the first sleeve 108.

A return lumen 118 formed in an annular space between an outer surface of the first sleeve 108 and an inner surface of the second sleeve 110 opens to the outside of the device 100 via a plurality of slots 130 extending through a screen 104 which is mounted over the distal end 106. The screen includes an opening 126 through which fluid from the distal opening 122 of the lumen 114 passes into the uterus. Negative pressure may be applied to the return lumen 118 to draw fluid from the region surrounding the distal end 106 through the screen 104 into the return lumen 118 for withdrawal from the body. In an alternative embodiment, a positive pressure may be applied through the lumen 114 elevating the pressure within the uterus and forcing fluid out of the uterus through the screen 104 and into the distal end 124 of the return lumen 118. After removal from the body, the fluid from the return lumen 118 may be filtered, reheated and returned to the uterus via the lumen 114 or may be withdrawn from circulation and replaced by fresh fluid as desired. The screen 104 facilitates the return of this fluid by providing an initial filtering of the fluid to reduce particles suspended therein. In one embodiment, an area of the return lumen 118 may be approximately 0.009 sq. inches.

An insulative gap 120 is formed in an annular space between an inner surface of the third sleeve 112 and an outer surface of the second sleeve 110. The insulative gap 120 may be filled with air to minimize heat transfer from the fluids flowing through the inlet lumen 114 and the fluid return lumen 118 to non-targeted tissue adjacent to the device 100 to prevent burns and/or other damage to this surrounding tissue. It will be understood by those of skill in the art that the second sleeve 110, which forms part of insulative gap 120, may be formed of a plastic or other thermally insulative material. As would be understood by those skilled in the art, one or more additional layers of insulation may be provided if desired.

As shown in FIG. 2, the first sleeve 108 extends distally past the second sleeve 110 such that an opening 122 of the inlet lumen 114 is distally beyond a distal opening 124 of the return lumen 118. Thus, fluid entering the return lumen 118 will do so via the screen 104 at locations proximal of the distal opening 122 of the lumen 114. it will be understood by those of skill in the art that a staggered flow pattern is established such that all of the fluid flow through the inlet lumen 114 is forced into the uterus and back to the return lumen 118. This staggered flow pattern creates greater turbulence within the uterus and allows for better heat distribution through the uterus. The screen 104 is coupled to the distal end 106 of the device such that a distal end 126 of the screen 104 is substantially aligned with the opening 122 of the inlet lumen 114 formed by the first sleeve 108. The screen 104 may be coupled to the longitudinal member 102 by any number of coupling means. For example, the screen 104 may include a male mating component 132 that is receivable within the insulative gap 120 between the second and third sleeves 110, 112, which acts as a female mating component. The male mating component 132 and the female mating component of the insulation gap 120 may be locked together.

Figure 4:
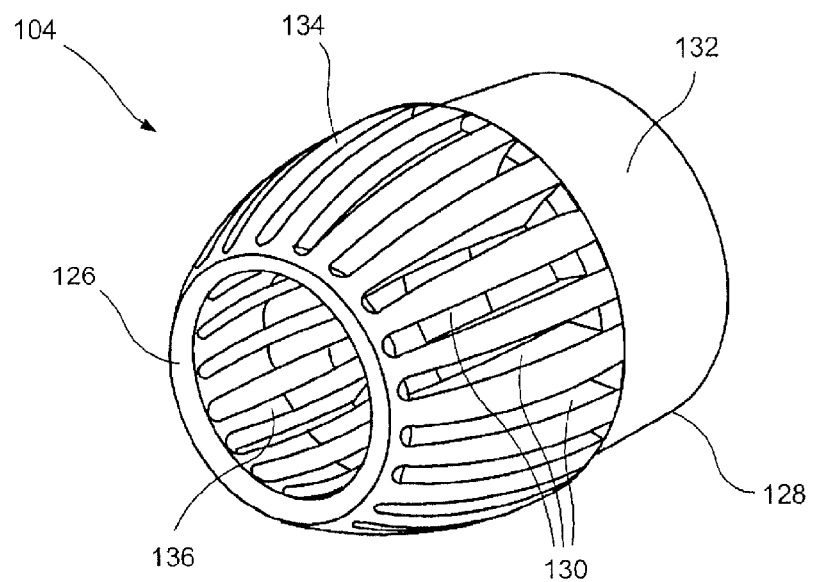
FIG. 4 shows a perspective view of a distal end of the device of FIG. 1.

As shown in FIG. 4, the screen 104 includes an open distal end 126 substantially similar in diameter to a diameter of the inlet lumen 114. The screen 104 is substantially dome-shaped with an outer surface of the screen 104 curved and a proximal end 128 of the screen 104 shaped to be received within the insulative gap 120 between the inner surface of the third sleeve 112 and the outer surface of the second sleeve 110. During endometrial ablation procedures, the cervix is generally dilated to approximately 8 mm to reduce the force required to insert an HTA device therethrough. As would be understood by those skilled in the art, the dome shape of the screen 104 and the tapered distal end 126 reduce the force required to insert the device 100 into the body possibly allowing the insertion of the device 100 with a lesser amount of dilation reducing trauma to the surrounding tissue. Additionally, the dome shape of the screen 104 may increase the structural stability of the screen 104, as loads during insertion are distributed substantially evenly around a circumference of an outer surface of the screen 104. It will be understood by those of skill in the art, however, that although the screen 104 is shown to be dome-shaped, the screen 104 may take a variety of shapes. These shapes will generally include a taper with the distal opening 126 being smaller than the proximal end 128 to facilitate insertion. For example, the screen 104 may be hemispherically shaped to provide an optimal level of strength. In an alternative embodiment, the screen 104 may have a truncated conical shape to facilitate insertion into the cervical cavity. In yet another embodiment, the screen 104 may be have a substantially parabolic dome shape such that the screen 104 may retain a level of strength, while still facilitating insertion into the cervical cavity.

The distal end 126 of the screen 104 extends from a distal end 138 of the first sleeve 108 proximally past a distal end 140 of the second sleeve 110 such that return fluid must first pass through the screen 104 to access the opening 124 of the return lumen 118. The screen 104 includes a plurality of slots 130 distributed around at least a portion of a circumference thereof with each slot extending along at least a portion of the length of the screen 104 (i.e., parallel to a longitudinal axis of the device 100) and passing from an opening in an outer surface 134 through an inner surface 136 of the screen 104. A width of each slot 130 may be made smaller than a width of the return lumen 118 to ensure that any debris that is able to pass through the screen 104, is too small to occlude the return lumen 118. As the screen 104 extends distally past the distal end of the second sleeve 110, the slots 130 increase the total area available for fluid to enter the return lumen 118 without substantially affecting the pressure in the return lumen 118. In a preferred embodiment, the aggregate area of the slots 130 is approximately five times the cross-sectional area of the return lumen 118. For example, if the cross-sectional area of the return lumen 118 is approximately 0.009 sq. inches, the aggregate area of the slots 130 may be approximately 0.05 sq. inches. This allows the pressure and the flow characteristics of the return lumen 118 to remain acceptable even if 80% or more of the screen 104 were occluded with debris. Additionally as will be understood by those of skill in the art, the distribution of the total area of the slots 130 over the surface of the screen 104 reduces the velocity and pressure with which fluid first contacts the longitudinal member 102 reducing the likelihood of large debris becoming embedded within the slots 130.

Figure 5:
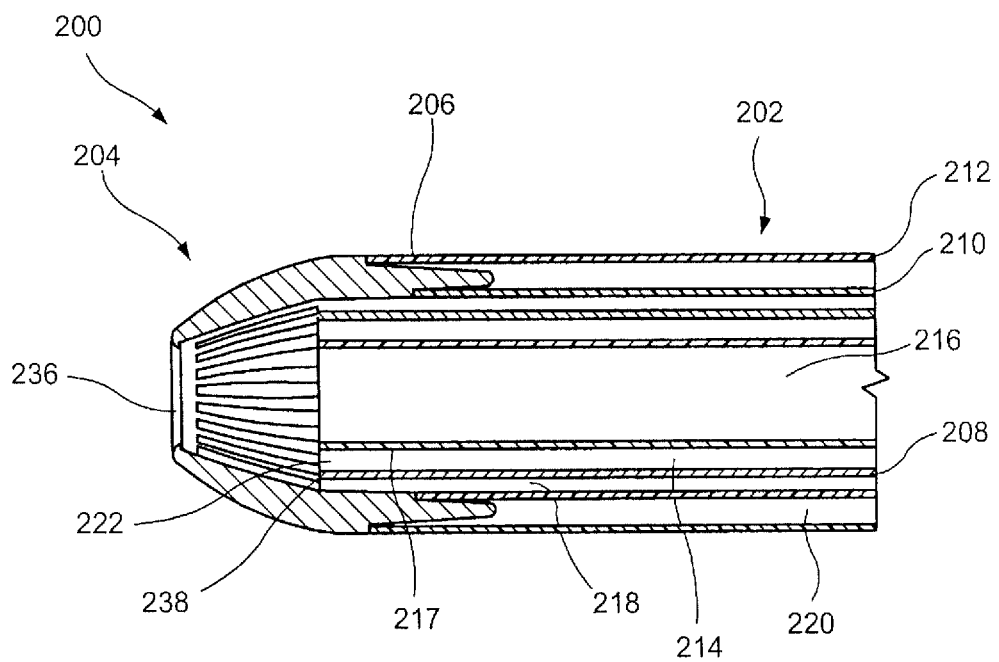
FIG. 5 shows a longitudinal cross-sectional view of a device according to a second exemplary embodiment of the present invention.
Figure 6:
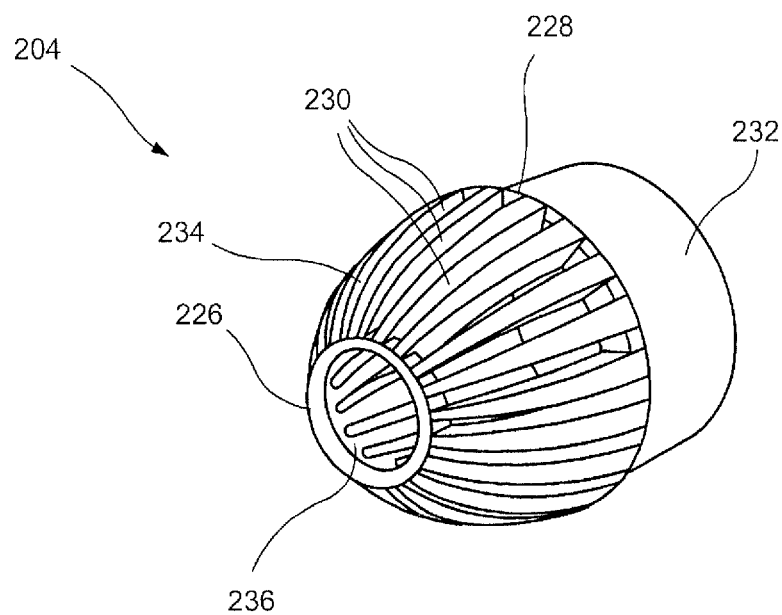
FIG. 6 shows a perspective view of a distal end of the device shown in FIG. 5.

As shown in FIGS. 5-6, a device 200 according to another embodiment of the present invention comprises a longitudinal member 202 and a screen 204 coupled to a distal end 206 thereof. Similarly to the device 100, the longitudinal member 202 includes a first sleeve 208, a second sleeve 210, and a third sleeve 212, each of which share a longitudinal axis. In the device 200, the first sleeve 208 extends slightly distally of the second and third sleeves, 210 and 212, respectively, with an outer wall of a distal portion of the return lumen 218 being formed by an inner surface of a mating component 232 of the screen 204. The mating component 232 is received within an annular space 220 between the outer surface of the second sleeve 210 and an inner surface of the third sleeve 212 and extends distally to a screen portion 234 of the screen 204. As described above, this annular space 220 serves as an insulation gap minimizing heat transfer between the heated fluids in the longitudinal member 202 and surrounding tissue. When mated to the longitudinal member 202, the mating component 232 ends at a point substantially aligned with the distal end 238 of the first sleeve 208 so that the return lumen 218 terminates at a point aligned with the distal opening 222 of the working channel 214. As shown in FIG. 5, the working channel 214 is sized so that, when a hysteroscope 216 is inserted therein, an annular space surrounding the hysteroscope 216 functions as an inlet lumen 217 for the device 200.

The screen 204 may be substantially similar to the screen 104. A distal opening 226 of the screen 204, however, may be smaller than the distal opening 126 and the mating component 232 of the screen 204 may mate with the longitudinal member 202 such that a proximal end 228 of the screen portion 234 substantially aligns with the distal end 238 of the first sleeve 208. The screen 204 covers the entire distal end 206 of the longitudinal member 202 to prevent debris from entering the debris lumen 218. It will be understood by those of skill in the art, that the aggregate area of the slots 230 is preferably substantially greater than an aggregate cross-sectional area of the inlet and return lumens 217, 218, respectively, so that the flow characteristics of these lumens may remain unchanged even when a significant portion of the area of the slots 230 is blocked by debris removed from the return fluid.

As shown in FIG. 6, the screen 204 includes a plurality of slots 230 substantially similar to the slots 130 of screen 104. The slots 230 extend around at least a portion of a circumference of the screen 230, and each slot 230 may extend along at least a portion of a length of the screen 204. A width of each of the slots 230 is preferably smaller than a width of the opening 224 of the return lumen 218 so that any debris that passes through the screen 204 via the slots 230 will be too small to occlude the return lumen 218.

Figure 7:
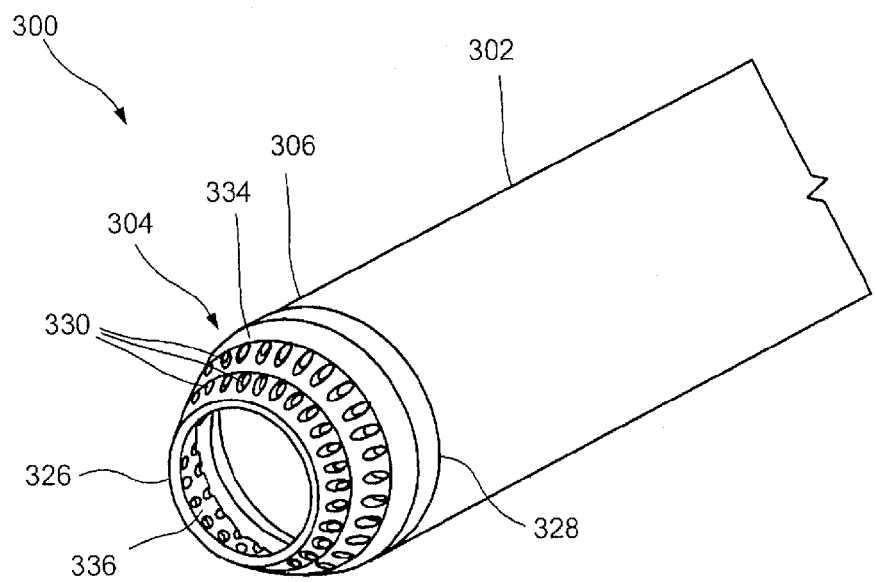
FIG. 7 shows a perspective view of a device according to a third exemplary embodiment of the present invention.

As shown in FIG. 7, a device 300, according to an alternate embodiment of the present invention, comprises a longitudinal member 302 and a screen 304 coupled to a distal end 306 thereof. The longitudinal member 304 may be substantially similar to either of the longitudinal members 102 and 202, respectively, described above in regard to devices 100, 200. The screen 304 may also be substantially similar to the screens 104 and 204, including an open distal end 326 that is smaller in diameter than a proximal end 328 of the screen 304. It will be understood by those of skill in the art that although the screen 304 is shown to be substantially conically shaped, the screen 304 may take a variety of shapes so long as the distal opening 326 is smaller than the proximal end 328. For example, the screen 304 may be dome-shaped.

The screen 304 further includes a plurality of holes 330 distributed around at least a portion of a circumference and a portion of a length of the screen 404. Each of the holes 330 extends from an outer surface 334 to an inner surface 336 such that return fluid must pass through the holes 330 to access a return lumen (not shown). Each of the holes 330 may be smaller in size than an opening of the return lumen to ensure that any debris that is able to pass through the holes 330 are too small to occlude the return lumen. It will be understood by those of skill in the art, that the aggregate area of the holes 330 is preferably substantially greater than an aggregate cross-sectional area of the inlet and return lumens of the longitudinal member 302 so that the flow characteristics of these lumens may remain unchanged even when a significant portion of the area of the holes 330 is blocked by debris removed from the return fluid.

Figure 8:
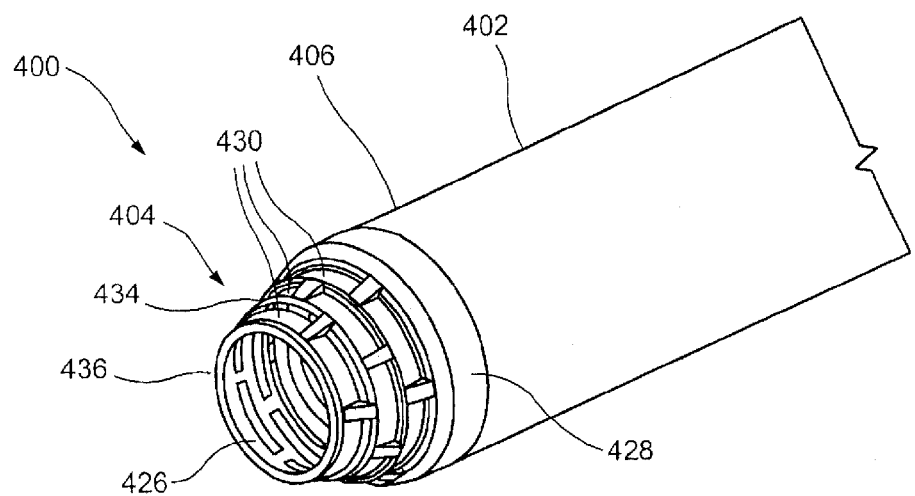
FIG. 8 shows a perspective view of a device according to a fourth exemplary embodiment of the present invention.

As shown in FIG. 8, a device 400, according to an alternate embodiment of the present invention, comprises a longitudinal member 402 and a screen 404 attached to a distal end 406 thereof. The longitudinal member 402 may be substantially similar to either of the longitudinal members 102 and 202, respectively, described above in regard to devices 100, 200. The screen 404 may also be substantially similar to the screens 104, 204 and 304, including an open distal end 426 that is smaller in diameter than a proximal end 428 of the screen 404. It will be understood by those of skill in the art that although the screen 404 is shown to be substantially conically shaped, the screen 404 may take a variety of shapes. As indicated above, tapered shapes may be desired to facilitate insertion. For example, the screen 404 may be dome-shaped, conic, etc.

The screen 404 further includes a plurality of slots 430 distributed along at least a portion of a length of the screen 404, each of the slots 430 extending around at least a portion of a circumference of the screen 404. Each of the slots 430 extends from an outer surface 434 to an inner surface 436 such that return fluid must pass through the slots 430 to access a return lumen (not shown). Each of the slots 430 may be smaller in width than opening of the return lumen to ensure that any debris that is able to pass through the slots 430 is too small to occlude the return lumen. It will be understood by those of skill in the art, that the aggregate area of the holes 430 is preferably substantially greater than an aggregate cross-sectional area of the inlet and/or return lumens of the longitudinal member 402 so that the flow characteristics of these lumens may remain unchanged even when a significant portion of the area of the slots 430 is blocked by debris removed from the return fluid.

It will be understood by those of skill in the art that various modifications and variations can be made in the structure and the methodology of the present invention without departing from the sprit or the scope of the invention. Thus, it is intended that the present invention cover the modifications and the variations of this invention provided that they come within the scope of the appended claims and their equivalents.

What is claimed is:

1. A method for circulating fluid to a target site within a living body, comprising:

supplying fluid to the target site via an inlet lumen of a longitudinal member of a circulating device, the longitudinal member including a first sleeve defining a working channel extending therethrough to a distal opening and a second sleeve extending therearound, the first sleeve including a first elongated structure and the second sleeve including a second elongated structure; and withdrawing fluid from the target site via a return lumen of the longitudinal member of the circulating device, the return lumen surrounding the inlet lumen, the fluid being withdrawn through a screen coupled to a distal end of the longitudinal member, the screen including a plurality of openings extending therethrough from a radially inner surface forming a radially outer wall of a distal portion of the return lumen to an outer surface thereof, wherein, in an operative configuration, a distal end of the first sleeve extends distally beyond a distal end of the second sleeve, and is located proximal to a distal tip of the screen, so that an opening of the inlet lumen is adjacent to a distal opening in the screen.

2. The method of claim 1, wherein an inner surface of the second sleeve is spaced from an outer surface of the first sleeve by an annular space forming the return lumen.

3. The method of claim 2, wherein the longitudinal element further comprises a third sleeve an inner surface of which is separated from an outer surface of the second sleeve by an insulating gap.

4. The method of claim 3, wherein the screen includes a mating portion extending
into a distal portion of the insulating gap to couple to the longitudinal member.

5. The method of claim 1, wherein at least a portion of the plurality of openings in the screen is formed as slots distributed around a circumference thereof.

6. The method of claim 5, wherein the slots extend substantially parallel to a
longitudinal axis of the longitudinal member.

7. The method of claim 5, wherein the slots extend substantially perpendicular to a longitudinal axis of the longitudinal member.

8. The method of claim 1, wherein each of the plurality of openings is a hole.

9. The method of claim 1, wherein an aggregate area of the plurality of openings is greater than a cross-sectional area of the return lumen.

10. The method of claim 9, wherein the aggregate area of the plurality of openings is at least four times the cross-sectional area of the return lumen.

11. The method of claim 10, wherein the aggregate area of the plurality of openings is at least five times the cross-sectional area of the return lumen.

12. The method of claim 1, wherein a distal end of the first sleeve substantially aligns with a distal end of the second sleeve such that an opening of the inlet lumen is substantially aligned with an opening of the return lumen.

13. The method of claim 1, wherein a diameter of the distal opening of the screen is substantially the same as a diameter of the working channel.

14. The method of claim 1, wherein the screen includes a tapered shape such that a diameter of a distal end of the screen is smaller than a diameter of a proximal end of the screen.

15. The method of claim 14, wherein the tapered shape is one of a parabolic dome, truncated cone, or a hemisphere.

* * * * *